(12) United States Patent
Breznock

(10) Patent No.: US 10,806,483 B2
(45) Date of Patent: *Oct. 20, 2020

(54) STEERABLE ENDOLUMINAL PUNCH

(71) Applicant: Indian Wells Medical, Inc., Laguna Beach, CA (US)

(72) Inventor: Eugene M. Breznock, Winters, CA (US)

(73) Assignee: Indian Wells Medical, Inc., Lake Forest, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/047,542

(22) Filed: Jul. 27, 2018

(65) Prior Publication Data

US 2018/0333170 A1 Nov. 22, 2018

Related U.S. Application Data

(63) Continuation of application No. 15/270,753, filed on Sep. 20, 2016, now Pat. No. 10,034,686, which is a continuation of application No. 13/944,448, filed on Jul. 17, 2013, now Pat. No. 9,445,836, which is a continuation of application No. 12/785,309, filed on May 21, 2010, now Pat. No. 8,491,619, which is a (Continued)

(51) Int. Cl.
| | |
|---|---|
| *A61B 17/3205* | (2006.01) |
| *A61B 17/00* | (2006.01) |
| *A61B 17/34* | (2006.01) |
| *A61B 18/00* | (2006.01) |
| *A61B 17/32* | (2006.01) |

(52) U.S. Cl.
CPC .. *A61B 17/32053* (2013.01); *A61B 17/00234* (2013.01); *A61B 17/34* (2013.01); *A61B 17/3478* (2013.01); *A61B 17/3496* (2013.01); *A61B 17/3415* (2013.01); *A61B 17/3468* (2013.01); *A61B 2017/003* (2013.01); *A61B 2017/00247* (2013.01); *A61B 2017/00331* (2013.01); *A61B 2017/320044* (2013.01); *A61B 2018/0038* (2013.01); *A61B 2018/00357* (2013.01); *A61B 2018/00392* (2013.01)

(58) Field of Classification Search
CPC .............. A61B 17/34; A61B 17/00234; A61B 17/3468; A61B 17/3415; A61B 2017/003; A61B 2017/00247; A61B 2018/00392
See application file for complete search history.

(56) References Cited

U.S. PATENT DOCUMENTS

| | | |
|---|---|---|
| 5,725,512 A | 3/1998 | Swartz et al. |
| 6,471,697 B1 | 10/2002 | Lesh |

(Continued)

*Primary Examiner* — Ashley L Fishback
(74) *Attorney, Agent, or Firm* — Crockett & Crockett, PC; K. David Crockett, Esq.

(57) ABSTRACT

A transseptal punch with a steering mechanism within the punch, such that punch can be steered and deflected within a guide catheter during delivery, to avoid skiving of the guide catheter inner wall by passage of the punch tip through the guide catheter. The punch can be advanced through a body lumen in its straight configuration and then be selectively articulated or curved to permit negotiation of tortuous curvature or to permit optimal approach or access to a puncture site. The punch is able to create holes in the atrial septum of the heart or other structures and is easier to use than punches that are pre-curved near their distal tip since it is easier to advance through accessory catheters.

2 Claims, 6 Drawing Sheets

Related U.S. Application Data continuation of application No. 11/492,328, filed on Jul. 24, 2006, now abandoned.

(60) Provisional application No. 60/702,239, filed on Jul. 25, 2005.

(56) References Cited

U.S. PATENT DOCUMENTS

| | | | |
|---|---|---|---|
| 6,650,923 | B1 | 11/2003 | Lesh et al. |
| 6,652,491 | B1 | 11/2003 | Walker et al. |
| 6,695,814 | B2 | 2/2004 | Greene et al. |

STEERABLE ENDOLUMINAL PUNCH

This application is a continuation of U.S. application Ser. No. 15/270,733, filed Sep. 20, 2016, now U.S. Pat. No. 10,034,686, which is a continuation of U.S. application Ser. No. 13/944,448, filed Jul. 17, 2013, now U.S. Pat. No. 9,445,836, which is a continuation of U.S. application Ser. No. 12/785,309, filed May 21, 2010, now U.S. Pat. No. 8,491,619, which is a continuation of U.S. application Ser. No. 11/492,328, filed Jul. 24, 2006, which in turn claims priority benefit under 35 USC § 119(e) to U.S. Provisional Application No. 60/702,239, filed Jul. 25, 2005, the entire contents of which are hereby incorporated herein by reference.

FIELD OF THE INVENTION

The invention relates to devices and methods for performing endovascular access to the cardiovascular system or other body vessels or body lumens, especially procedures performed in the fields of cardiology, radiology, electrophysiology, and surgery.

BACKGROUND OF THE INVENTION

During certain interventional procedures that are directed at cardiac access, the patient is catheterized through an access point in a vein or artery. A catheter is routed to the heart or other region of the cardiovascular system through the access point, which may be created by a cutdown or a percutaneous access procedure. The catheter may be routed to a target location within the heart, cerebrovasculature, or other region of the cardiovascular system. In certain cases, it becomes necessary to create a hole in a cardiovascular structure so that catheters or devices can be routed through a wall so as to provide for placement on the other side of the wall. One such case is the need to punch a hole in the septum that divides the right atrium of the heart from the left atrium. Such atrial septal punctures are increasingly used to gain access to the left atrium by way of the central venous system and the right atrium. Access to the left atrium of the heart is often useful in therapeutic and diagnostic procedures such as, but not limited to, valve replacement, valve repair, electrophysiology mapping, cardiac ablation, atrial appendage plug placement, and the like.

The currently accepted procedure for left atrial access involves routing a needle called a Brockenbrough™ needle into the right atrium with the Brockenbrough needle pre-placed within a guiding catheter. The guiding catheter specifically preferred for use with a Brockenbrough needle is called a Mullins™ catheter. The Brockenbrough needle is a long punch formed from a stainless steel wire stylet that is surrounded by a stainless steel tube. The distal end of the stainless steel tube forms a relatively sharp circular punch capable of penetrating certain vascular structures such as the inter-atrial septum. Brockenbrough needle stylets are typically 0.013 to 0.014 inches in diameter while the stainless steel tube is generally between 0.045 and 0.050 inches in outside diameter. The Brockenbrough needle outside diameter is configured to slidingly fit within the central lumen of the Mullins catheter. The stainless steel tube is substantially straight along most of its length but is pre-bent into a curved or "J" shape at its distal end. A loop at the proximal end of the Brockenbrough stylet facilitates grasping of the stylet and performing manual advance or retraction. The current art considers the access to the right atrium from the femoral vein to be relatively straight so the current devices are straight except for the distal curve, which is shaped for the approach to the atrial septal wall.

The Brockenbrough needle, a relatively rigid structure, is operated by advancing the device, with its stylet wire advanced to blunt the sharp tip, within its guiding catheter through the inferior vena cava and into the superior vena cava. Under fluoroscopic guidance, the Brockenbrough needle, retracted inside the distal tip of the Mullins catheter, is withdrawn caudally into the right atrium until it falls or translates medially into the Fossa Ovalis. The force of the Brockenbrough needle/Mullins catheter assembly pushing against the relatively weak atrial septal wall causes the Fossa Ovalis to become tented toward the left atrium. The Brockenbrough needle, protected by the blunt distal tip of the Mullins catheter, is firmly held against the Fossa Ovalis of the atrial septum. Pressure monitoring and dye injection are carried out through the central lumen of the punch following removal of the stylet wire. The circular or hollow punch is next advanced distally to puncture a hole through the atrial septum. Erroneous placement of the punch can lead to penetration of adjacent structures such as the aorta, damage to which would cause potentially severe hemorrhage and potentially compromise the health of the patient. Thus, extreme care is exercised to verify location prior to the actual punching step. The Brockenbrough needle is next advanced through the atrial septum. The guide catheter, which includes a removable, tapered, distal dilator, having a central lumen for the Brockenbrough needle, is advanced over the Brockenbrough needle system and into the left atrium. The Brockenbrough needle is next removed from the Mullins guide catheter along with the central dilator or obturator.

A main disadvantage of this system is that the Brockenbrough needle system is pre-curved at its distal end and is relatively rigid. This pre-curving, rigidity, and necessary distal sharpness causes the Brockenbrough needle system to carve material from the interior wall of the otherwise straight guiding catheter when the Brockenbrough needle assembly is inserted therethrough. The material carved from the guide catheter could potentially be released into the cardiovascular system and generate emboli with any number of serious clinical sequelae. Should this embolic catheter material enter the left atrium it could flow into and block important arterial vasculature such as the coronary arteries or cerebrovasculature. Furthermore, advancing a pre-curved, rigid punch through the cardiovascular system is difficult and could potentially damage the vessel wall or any number of significant cardiovascular structures, during the advancement.

It would be desirable to have a Brockenbrough needle system that was initially straight and then became curved after being inserted into the guiding catheter. Such a straight Brockenbrough configuration would be advantageous during ex-vivo insertion as well as insertion after the guide catheter has already been placed into the cardiovascular system. During ex-vivo insertion, the debris can be flushed from the lumen of the guide catheter but complete removal is not assured and emboli can still be generated by the device. However, if the guide catheter was already inserted into the cardiovascular system, the debris could not be flushed out ahead of time and could easily flow toward or be released into the cardiovascular system with potentially catastrophic or fatal results. Furthermore, the needle or punch could be more easily advanced into the body lumen if it were not pre-curved.

SUMMARY OF THE INVENTIONS

In an embodiment, the invention is a transvascularly or endovascularly placed tissue punch, with internal deflect-ability or the ability to articulate, at its distal end, in a direction away from its longitudinal axis. The punch can also be termed a catheter, needle, or cannula. The punch is generally fabricated from stainless steel and comprises an outer tube, an inner tube, a central stylet wire, and a distal articulating region. The deflecting or articulating mechanism is integral to the punch. The punch, needle, or catheter is sufficiently rigid, in an embodiment, that it can be used as an internal guidewire or internal guide catheter. The punch is useful for animals, including mammals and human patients and is routed through body lumens or other body structures to reach its target destination.

In an embodiment, the punch comprises an inner core wire or stylet, an inner tube and an outer tube. In an embodiment, the stylet can be removable or non-removable. The punch further comprises a hub at its proximal end which permits grasping of the punch and also includes a stopcock or valve to serve as a lock for the stylet, or inner core wire, as well as a valve for control of fluid passage into and out from the innermost lumen within which the stylet or inner core wire resides. The proximal end further comprises one or more control handles to manipulate the amount of articulation at the distal end of the catheter. The proximal end further is terminated with a female Luer or Luer lock port, which is suitable for attachment of pressure monitoring lines, dye injection lines, vacuum lines, a combination thereof, or the like.

The punch is fabricated so that it is substantially straight from its proximal end to its distal end. Manipulation of a control mechanism at the proximal end of the punch causes a distal region of the punch to bend or curve away from its longitudinal axis. The bending, steering, or articulating region is located near the distal end of the punch and can be a flexible region or structure placed under tension or compression by pull wires or control rods routed from the control handle at the proximal end of the punch to a point distal to the flexible region. In another embodiment, the bending or articulating mechanism can also be created by pre-bending the outer tube in one direction and bending the inner tube in another direction. The two tubes can be rotated relative to each other, about their longitudinal axis, by turning knobs or grips at the proximal end of the punch. When the curvatures of both tubes are aligned, the tubes will generally cooperate and not oppose each other, thus, maximum curvature or deflection is generated. When the tubes are rotated so their natural curvatures are aligned 180 degrees from each other, the curves will oppose each other or cancel out. Thus, the nested tubes will be substantially straight when the curvatures of the two concentric tubes oppose each other. Alignment marks or graduations at the proximal end can be used to assist with proper rotational alignment of the two tubes. The central core wire or stylet is generally straight and flexible and does not contribute to the curvature. In another embodiment, however, the stylet can be imparted with a curvature to assist with steering or articulation. Rotation of the two concentric tubes at relative angles between 180 degrees and 0 degrees will result in intermediate amounts of deflection so the amount of deflection can be increased or decreased in an analog, continuously variable, digital, or stepwise fashion. The stepwise or digital response can be generated using detents or interlocks that weakly engage at specific pre-determined locations. A locking mechanism can be further utilized to hold the two tubes in rotational alignment once the desired amount of curvature has been achieved.

In another embodiment, steerability can be obtained using actuators on the surface or within the interior of the cannula to force bending of the cannula. These actuators can be typically electrically powered. In an embodiment, an actuator can comprise electrical leads, a power source, a compressible substrate, and shape memory materials such as nitinol. Such actuators may be distributed along the length of the cannula. The actuators may be placed so as to oppose each other. Opposing actuators are activated one at a time and not simultaneously and can generate a steering effect or back and forth motion.

Other embodiments of the inventions comprise methods of use. One method of use involves inserting the central core wire so that it protrude out the distal end of the punch. A percutaneous or cutdown procedure is performed to gain access to the vasculature, either a vein or an artery. An introducer and guidewire are placed within the vasculature and the guidewire is routed proximate to the target treatment site. The introducer can be removed at this time. A guiding catheter, preferably with a central obturator or dilator is routed over the guidewire to the target site. In an embodiment, the target site can be the atrial septum. The guidewire can be removed at this time. The punch is adjusted so that it assumes a substantially straight configuration. The punch can be advanced through the central lumen of the already placed catheter. By making the punch as straight as possible, there is no curvature to force the sharpened distal edges of the punch to scrape the inside of the catheter lumen as the punch is advanced distally inside the guide catheter and potentially dislodge or scythe away debris or material which could cause embolic effects to the patient. Carefully ensuring that the punch does not protrude beyond the distal end of the catheter or its obturator, the punch is next deflected so that it forms a curve. The curve is oriented so that it is medially directed toward the atrial septum. Alignment with any curvature of the catheter can be completed at this time. The punch and guide catheter/obturator are withdrawn caudally, as a unit, into the right atrium. The punch and guide catheter are positioned using fluoroscopy or other imaging system against the Fossa Ovalis. The Fossa Ovalis is a relatively thin structure and the force of the punch will tent the Fossa Ovalis toward the left atrium. In one embodiment, the central core wire or stylet, initially advanced, can next be withdrawn to expose the sharp distal edge of the punch. When correctly positioned under fluoroscopy, ultrasound, or other imaging system, dye can be injected into the central lumen of the punch at its proximal end and be expelled out of the distal end of the punch and obturator to paint or mark the Fossa Ovalis. A generally "V-shaped" mark can be observed under fluoroscopy, which denotes the location of the Fossa Ovalis. The curvature of the punch can be increased or decreased by articulation to gain optimal alignment with the Fossa Ovalis. This steering function can be very beneficial in device placement.

Maintaining the position of the guiding catheter against the Fossa Ovalis, the punch is advanced distally against and through the atrial septum, in the region of the Fossa Ovalis, so that it penetrates and protrudes into the left atrium. In order to stabilize the atrial septal tissue prior to coring, a distally protruding corkscrew tipped wire or a vacuum head operably connected to the proximal end of the punch, can be used to grasp and retract the septal tissue. Once the initial penetration is completed, the guide catheter is next advanced, with its tapered obturator leading the way, across the atrial septum until it resides within the left atrium. The tapered obturator or dilator along with the punch can be removed at this time to allow for catheter placement through the guiding catheter. In another embodiment, a calibrated spacer can be used between the guide catheter hub and the punch hub to ensure that the punch does not protrude beyond the distal end of the guide catheter tip until the desired time for punching the hole. At this point, the spacer is unlocked and removed from the punch or catheter.

In another embodiment, the core wire or stylet is sharpened and serves as a tissue punch. In this embodiment, the distal end of the hollow tubes of the punch are blunted and made relatively atraumatic. Once the core wire punch has completed tissue penetration, the outer tubes are advanced over the central punch wire through the penetration and into the left atrium. In another embodiment, a pressure monitoring device such as a catheter tip pressure transducer, or a pressure line terminated by a pressure transducer, can be affixed to a quick connect, generally a Luer fitting, at the proximal end of the punch hub. By monitoring pressure, it is possible to determine when the distal end of the punch has passed from, for example, the right atrium into the left atrium, because the pressure versus time curves in these two chambers are measurably, or visually, different. The proximal end of the hub further has provision for attachment to a dye injection line for use in injecting radiographic contrast media through the central lumen of the punch. Typically a manifold can be attached to the Luer fitting on the proximal end of the hub, the manifold allowing for pressure monitoring, for example on a straight through port, and for radiopaque dye injection, for example through a side port. A stopcock, or other valve, can be used to control which port is operably connected to the central lumen of the punch.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF THE INVENTION

In accordance with current terminology pertaining to medical devices, the proximal direction will be that direction on the device that is furthest from the patient and closest to the user, while the distal direction is that direction closest to the patient and furthest from the user. These directions are applied along the longitudinal axis of the device, which is generally an axially elongate structure having one or more lumens or channels extending through the proximal end to the distal end and running substantially the entire length of the device.

Figure 1:
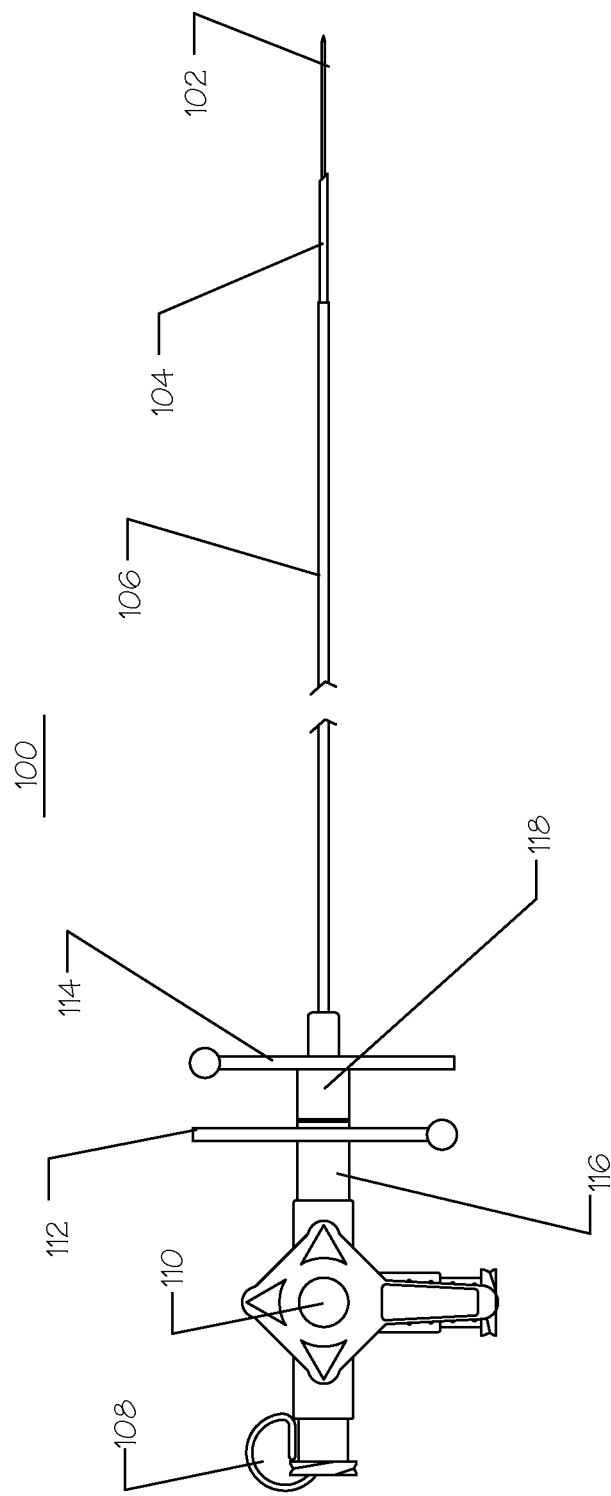
FIG. 1 illustrates a side view of a trans-septal punch assembled so that the inner tube is bent in a direction 180 degrees opposite that of the outer tube, resulting in a substantially straight punch configuration.

FIG. 1 illustrates a side view of a punch, needle, or catheter assembly 100, with an integral articulating or bending mechanism. The punch assembly 100 comprises a stylet or obturator wire 102, an inner tube 104, an outer tube 106, an obturator grasping tab 108, a stopcock 110, an inner tube pointer 112, an outer tube pointer 114, an inner tube hub 116, and an outer tube hub 118.

Referring to FIG. 1, the obturator wire 102 is affixed to the obturator grasping tab 108. The stylet or obturator wire 102 is inserted through the central lumen of the inner tube 104 and is slidably disposed therein. The stopcock 110 is affixed to the inner tube hub 116 and the through lumen of the stopcock 110 is operably connected to the central lumen of the inner tube 104. The inner tube pointer 112 is affixed to the inner tube hub so that it is visible to the user. The outer tube pointer 114 is affixed to the outer tube hub 118 so that it is visible to the user. The inner tube hub 116 and the inner tube 104 are able to rotate about the longitudinal axis within the outer tube hub 118 and the outer tube 106. In an embodiment, the inner tube 104 is restrained from longitudinal motion relative to the outer tube 106. In another embodiment, the inner tube 104 can be advanced distally relative to the outer tube 106. In this latter embodiment, advancement of the inner tube 104 can be used to facilitate punching. The distal end of the inner tube 104 can be sharpened and serve as a punch. The distal end of the inner tube 104 is sheathed inside the outer tube 106 to protect the tissue from the sharp distal edge of the inner tube 104 until the inner tube 104 is advanced distally outside the distal end of the outer tube 106. A releaseable lock can be used to maintain the axial or longitudinal position of the inner tube 104 relative to the outer tube 106 until punching is required. A releaseable lock can further be used to maintain the rotational position of the inner tube hub 116 and thus the inner tube 104 relative to the outer tube hub 118 and the outer tube 106.

All components of the punch assembly 100 can be fabricated from metals such as, but not limited to, stainless steel, Elgiloy™, cobalt nickel alloy, titanium, nitinol, or the like. The nitinol can be shape-memory or it can be superelastic. The metals used in the obturator wire 102, the inner tube 104 and the outer tube 106 are advantageously cold rolled, heat treated, or otherwise processed to provide a full spring hardness. The inner tube 104, the outer tube 106, or both, are relatively rigid, resilient structures. Polymeric materials, such as, but not limited to, polycarbonate, ABS, PVC, polysulfone, PET, polyamide, polyimide, and the like, can also be used to fabricate the stopcock 110, the inner tube hub 116, the outer tube hub 118, the inner tube pointer 112, and the outer tube pointer 114. The materials are beneficially radiopaque to maximize visibility under fluoroscopy during the procedure. Additional radiopaque markers fabricated from tantalum, platinum, iridium, barium sulfate, and the like can be added to improve visibility if needed. The inner tube 104 is curved or bent near its distal end into a gentle curve, preferably with a radius of between 1 to 5 inches and so that the distal tip is deflected through an angle of approximately 10 to 90 degrees from the longitudinal axis of the inner tube 104. The outer tube 106 is curved or bent near its distal end into a gentle curve, preferably with a radius of between 1 to 5 inches and so that the distal tip is deflected through an angle of approximately 10 to 90 degrees from the longitudinal axis of the outer tube 106. The inner tube hub 116 is welded, silver soldered, bonded, crimped, or otherwise fastened to the proximal end of the inner tube 104 so that the inner tube pointer 112 points in the direction of the bend in the inner tube 104. The outer tube hub 118 is welded, silver soldered, bonded, crimped, or otherwise fastened to the proximal end of the outer tube 106 so that the outer tube pointer 114 points in the direction of the bend in the outer tube 106. When the inner tube pointer 112 is oriented 180 degrees away from the direction of the outer tube pointer 114, the bend in the inner tube 104 substantially counteracts or opposes the bend of the outer tube 106 and the coaxial assembly 100 is substantially straight, as shown in FIG. 1. The stopcock 110 can also be a ring seal, Tuohy-Borst valve, membrane valve, hemostasis valve, gate valve, or other valve, generally, but not necessarily manually operated. The stiffness of the inner tube 104 and the outer tube 106 are sufficient that the punch can be used as a guide for other catheters through which the punch 100 is passed.

Figure 2:
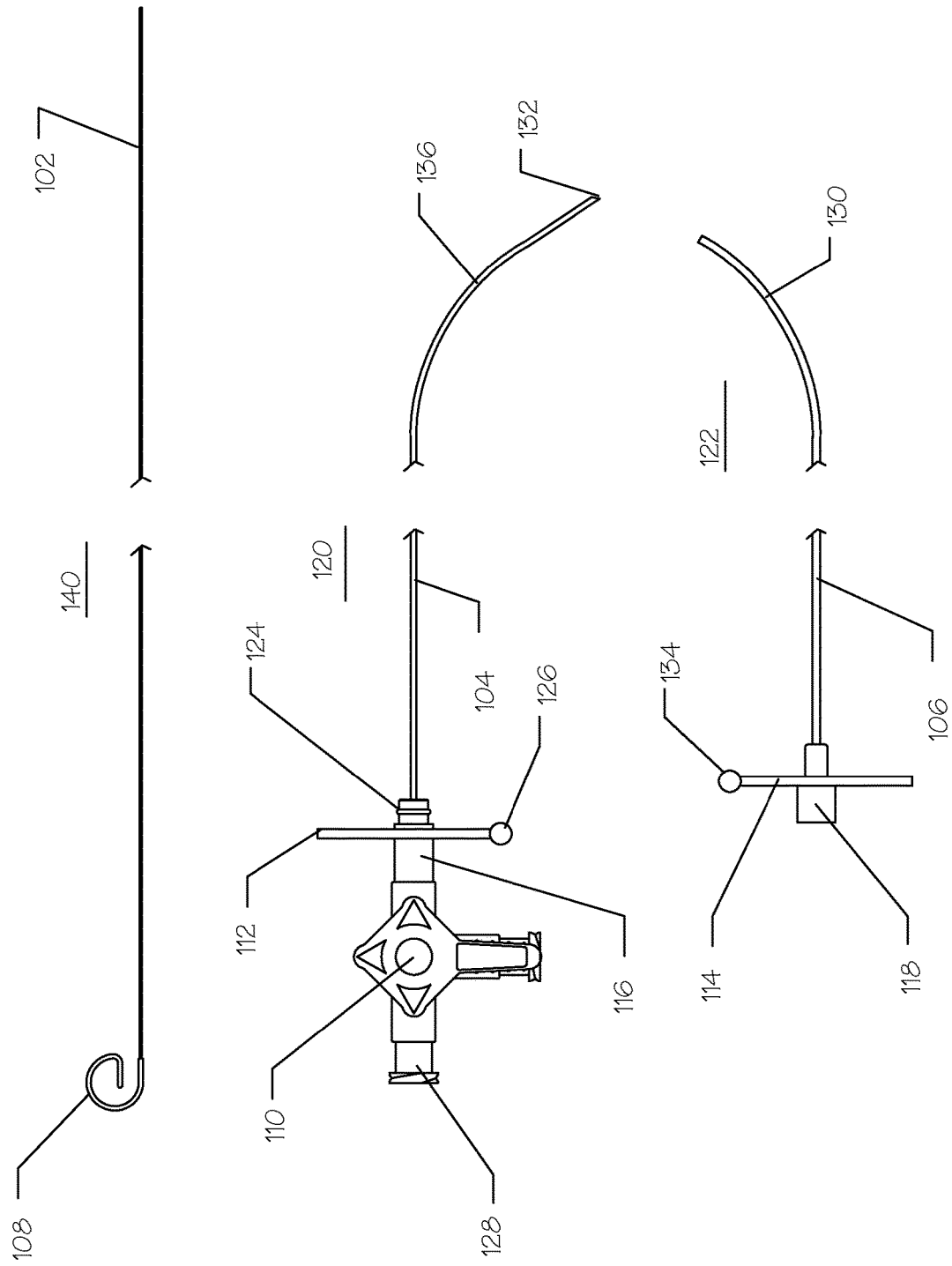
FIG. 2 illustrates a side view of the disassembled trans-septal punch showing the central core wire or stylet, the inner tube bent in one direction and the outer tube bent in another direction.

FIG. 2 illustrates a side view of a stylet or obturator 140 further comprising the obturator wire 102 and the obturator-grasping tab 108. The obturator wire 102 is blunted at its distal end to render it as atraumatic as possible. In another embodiment, the obturator wire 102 can be tapered in diameter to render it very flexible and therefore atraumatic at its distal end. The obturator wire 102, in another embodiment, can be sharpened and serve as a needle or primary punching mechanism. FIG. 2 also illustrates an intermediate punch assembly 120 further comprising the inner tube 104, the stopcock 110, the inner tube pointer 112, the inner tube hub 116, an inner tube seal 124, an inner tube pointer ball 126, a through lumen port 128, a beveled distal tip 132, and a pre-set curve 136. FIG. 2 further illustrates an outer tube assembly 122 further comprising the outer tube 106, the outer tube hub 118, the outer tube pointer 114, an outer tube distal curve 130, and an outer tube pointer ball 134.

Referring to FIG. 2, the obturator-grasping tab 108 is affixed, either integral to, silver soldered, welded, crimped, adhered, pinned, or otherwise attached, to the proximal end of the obturator wire 102. The inner tube 104 is affixed to the inner tube hub 116 by silver soldering, welding, potting, crimping, setscrew, pin, or other fixation method, such that the hub 116 rotates 1 to 1 with the inner tube 104. An optional inner tube pointer ball 126 is affixed to the inner tube pointer 112 and provides additional visual and tactile rotational positioning sense for the intermediate punch or needle assembly 120. A curve or bend 136 is heat set, or cold worked into the inner tube 104 at or near its distal end. The distal end of the inner tube 104 comprises a bevel 132 which helps serve as a punch or cutting edge for the inner tube 104. The angle of the bevel 132 can range between 20 and 70 degrees from the direction perpendicular to the longitudinal axis of the inner tube 104. In another embodiment, the bevel is removed and the distal tip of the inner tube 104 is a gentle inward taper or fairing moving distally that serves as a dilator should the obturator wire 102 be used as the punching device rather than the blunt distal tip obturator of the inner tube 104. The inner tube hub 116 further comprises a circumferential groove with an "O" ring 124 affixed thereto. The "O" ring 124 serves to form a fluid (e.g. air, blood, water) tight seal with the inner diameter of the outer sheath hub 118 central lumen and allows for circumferential rotation of the inner tube hub 116 within the outer tube hub 118. The "O" ring 124 is fabricated from rubber, silicone elastomer, thermoplastic elastomer, polyurethane, or the like and may be lubricated with silicone oil or similar materials. The stopcock 110 can be a single way or a three-way stopcock without or with a sideport, respectively.

The outer punch assembly 122 comprises the bend 130, which is heat set or cold worked into the outer tube 106 in the same longitudinal location as the bend 136 of the inner tube. The wall thicknesses of the inner tube 104 and the outer tube 106 are chosen to provide bending forces that cancel out when the curves 136 and 130 are oriented in opposite directions and the inner tube 104 is inserted fully into the outer tube 106. The wall thickness of the outer tube 106 and the inner tube 104 can range between 0.003 inches and 0.20 inches, preferably ranging between 0.004 and 0.010 inches. The outer diameter of the outer tube 106 can range between 0.014 and 0.060 inches and preferably between 0.025 and 0.050 inches. The outer diameter of the obturator wire 102 can range between 0.005 and 0.030 inches and preferably range between 0.010 and 0.020 inches.

Figure 3:
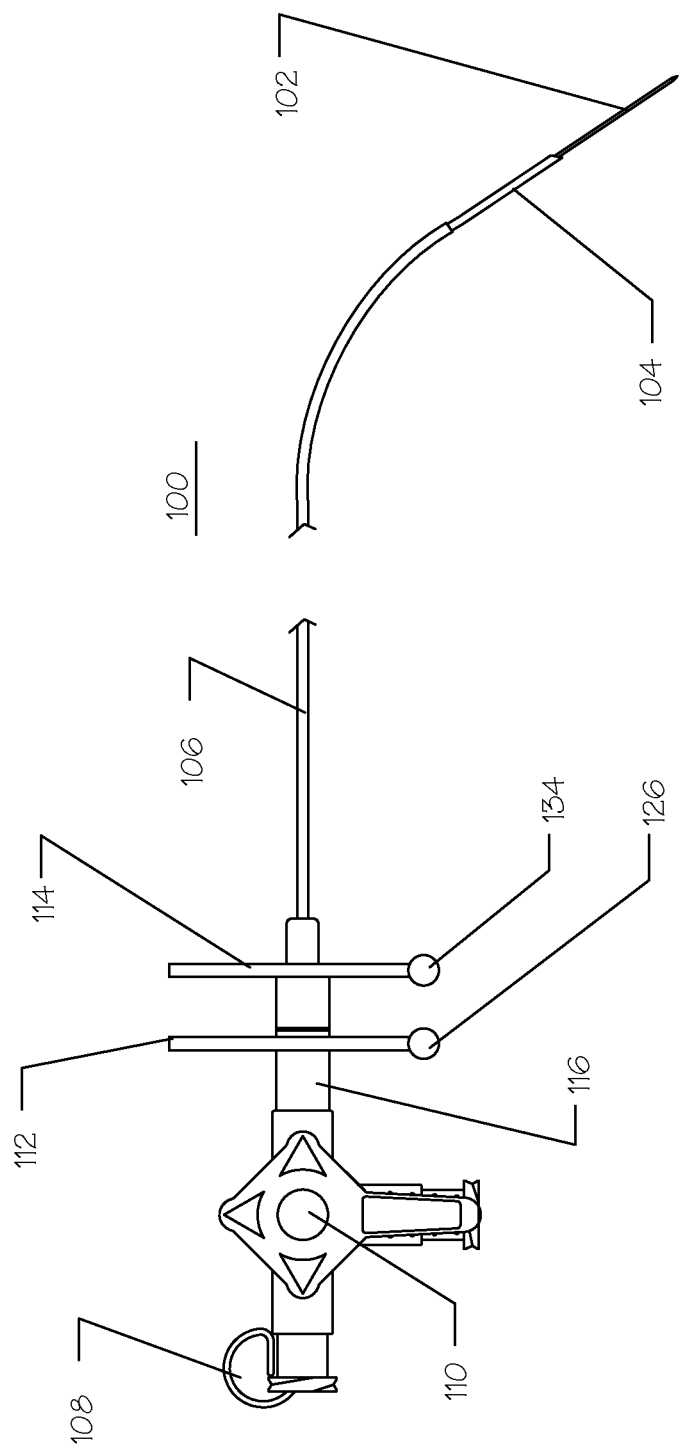
FIG. 3 illustrates a side view of the trans-septal punch assembled so that the inner tube bend is aligned in the same direction as the outer tube bend, resulting in a curved distal end on the punch assembly.

FIG. 3 illustrates a side view of the punch assembly 100 fully assembled and aligned so that both the inner tube distal curve 136 (Refer to FIG. 2) and the outer tube distal curve 130 are aligned in the same direction resulting in a natural bend out of the axis of the punch 100. The punch assembly 100 comprises the obturator wire 102, the inner tube 104, the outer tube 106, the obturator grasping tab 108, the stopcock 110, the inner tube pointer 112, the outer tube pointer 114, the inner tube hub 116, the inner tube pointer ball 126, and the outer tube pointer ball 134.

Referring to FIG. 3, the outer tube pointer 114 and inner tube pointer 112 are aligned together and in this configuration, the tubing assembly possesses its maximum curvature, which is oriented in the same directions as the pointers 112 and 114. The pointer balls 126 and 134 are aligned together to provide additional tactile and visual indices of curvature direction. In an embodiment, the curvature of the tube assembly 104 and 106 is unbiased with no net force exerted therebetween and an angle of approximately 45 degrees is subtended by the device in the illustrated configuration. Further curvature can also occur out of the plane of the page so that the curvature takes on a 3-dimensional shape, somewhat similar to a corkscrew. In another embodiment, the curvature of the aligned inner tube 104 and the outer tube 106 subtends an angle of 90-degrees or greater. Again, the inner tube 104 and the outer tube 106 have stiffness sufficient that the assembly is capable of guiding any catheter through which the punch 100 is passed. In another embodiment, the inner tube 104 and the outer tube 106 have different degrees of curvature so that when they are aligned, a net force still is generated between the two tubes, although a maximum curvature configuration is still generated. This embodiment can be advantageous in permitting articulation in a direction away from the direction of primary curvature.

The radius of curvature of the punch 100 can range from substantially infinity, when straight, to as little as 0.5-cm, with a preferred range of infinity to as little as 2-cm radius when fully curved or articulated. One embodiment permits a substantially infinite to a 3-cm radius of curvature. The overall working length of the punch, that length from the proximal end of the outer tube hub to the distal most end of the punch, can range from 10 to 150-cm and preferably between 60 and 100-cm, with a most preferred range of between 70 and 90-cm. A preferred curve has a radius of about 3-cm and is bent into an arc of about 45 to 90 degrees.

Figure 4:
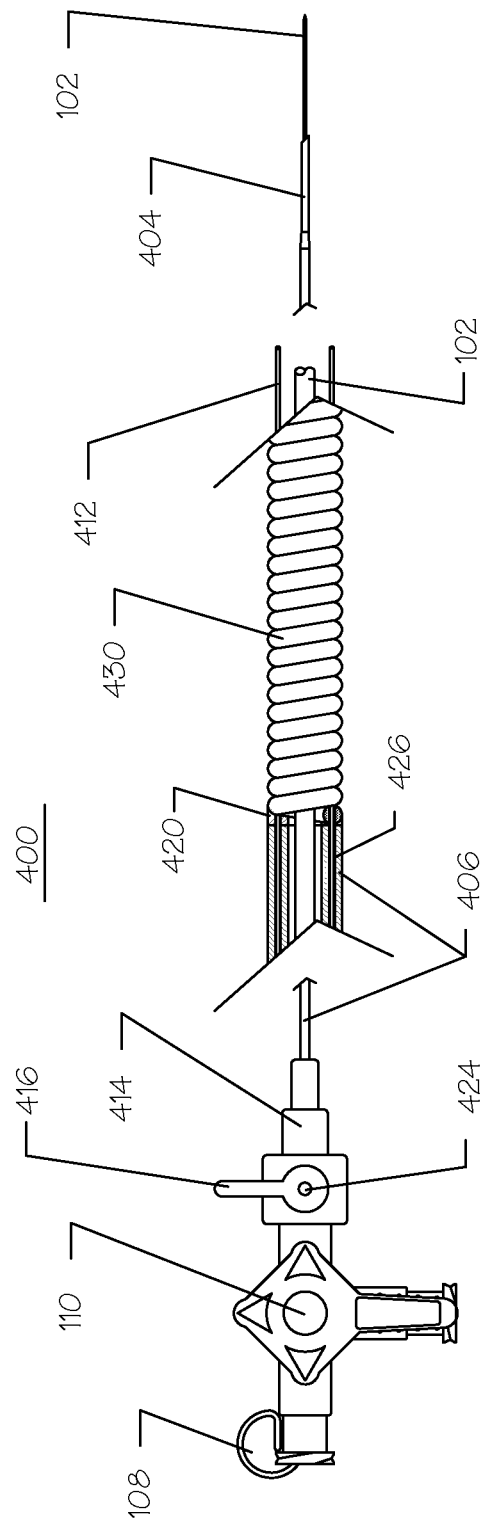
FIG. 4 illustrates a side view of a trans-septal punch comprising a flexible region proximal to the distal end and pull-wires disposed between the distal end and the proximal end of the punch.

FIG. 4 illustrates a side view of another embodiment of a needle or punch assembly 400 comprising an obturator wire 102, an obturator wire grasping tab 108, a stopcock 110, an inner tube 404, an outer tube 406, a plurality of deflecting wires 412, an outer tube hub 414, a deflecting lever 416, a weld 420, an axis cylinder 424, a plurality of deflecting wire channels 426, and a flexible region 430. The distal end of the region just proximal to the flexible region 430 is shown in breakaway view. Furthermore, the distal end of the region just proximal to the flexible region 430 as well as the flexible region 430 has been expanded in scale so that certain details are more clearly visible.

Referring to FIG. 4, the flexible region 430 is affixed to the outer tube 406 by a weld 420. The flexible region 430 can also be fixed to the outer tube 406 by a crimp, pin, setscrew, adhesive bond, interference fit, mechanical interlock, thread, or the like. The attachment between the flexible region 430 and the outer tube 406 is made at the proximal end of the flexible region 430 and a second attachment or weld 420 can be made at the distal end of the flexible region 430 so as to attach to a length of distal outer tube 406. The flexible region 430 can comprise a length of coiled wire such as that used in guidewires, it can be a tube that comprises cutouts to provide a backbone configuration to impart flexibility, it can be a length of polymeric tube with elastomeric characteristics, or it can be another type of structure that is known in the art as providing flexibility. These preferred structures also advantageously provide column strength and kink resistance to the flexible region 430. The center of the flexible region 430 is hollow and comprises a lumen, which is operably connected to the central lumen of the outer tube 406 at both the proximal and distal end of the flexible region 430. The stopcock 110 is affixed, at its distal end, to the outer tube hub 414. The outer tube hub 414 further comprises a deflecting lever 416 that is affixed to the axis cylinder 424, which serves as an axle or rotational pin, and can be moved proximally or distally by manual action on the part of the operator or by a motor or other electromechanical actuator (not shown). The deflecting lever 416 is operably connected to the proximal ends of the deflecting wires 412. In an exemplary embodiment, one of the deflecting wires 412 is affixed to the top of the axis cylinder 424 and the other deflecting wire is affixed to the bottom of the axis cylinder 424. When the deflecting lever is pulled proximally, for example, the top wire 412 is placed under tension and the tension on the bottom wire is relieved causing tension to be exerted on the distal end of the punch 400. The deflecting wires 412 are slidably routed through the deflecting wire channels 420 within the outer tube 406. The deflecting wires 412 also run through the deflecting wire channels 420 within the flexible region 430. The deflecting wires 412 can also be routed through the internal lumen of the outer tube 406 and the flexible region 430.

Referring to FIG. 4, the outer tube hub 414 is affixed to the proximal end of the outer tube 406 by a crimp, pin, setscrew, adhesive bond, interference fit, mechanical interlock, thread, or the like. The inner tube 404 is affixed to the distal end of the outer tube 406 by a crimp, pin, setscrew, adhesive bond, interference fit, mechanical interlock, thread, or the like. In another embodiment, the inner tube 404 is routed throughout the length of the outer tube 406. In this embodiment, the inner tube can comprise grooves (not shown) that serve as deflecting wire channels 420 when the inner tube 404 is inserted inside the outer tube 406. Such grooves can also be disposed on the interior surface of the outer tube 406, rather than on the exterior surface of the inner tube 404. The obturator wire 102 and the attached grasping loop 108 are slidably disposed within the inner lumen of the outer tube 406, or the inner tube 404. The inner tube 404 is gently tapered up to the outer tube 406 at the distal end of the outer tube 406 in a transition region so that a dilator effect can be created during distal advancement of the punch 400. The distal end of the inner tube 404 can comprise a bevel 132 (FIG. 2) or other sharp point for punching through biological tissue. The distal end of the inner tube 404 preferably forms a non-coring needle or punch that does not excise a tissue sample. The non-coring punch feature is achieved by keeping the central lumen closed or very small. The non-coring punch 400 embodiment can comprise filling the lumen of the inner tube 404 with the obturator or stylet wire 102 to prevent the sharp edge of the inner tube from functioning as a trephine.

Figure 5:
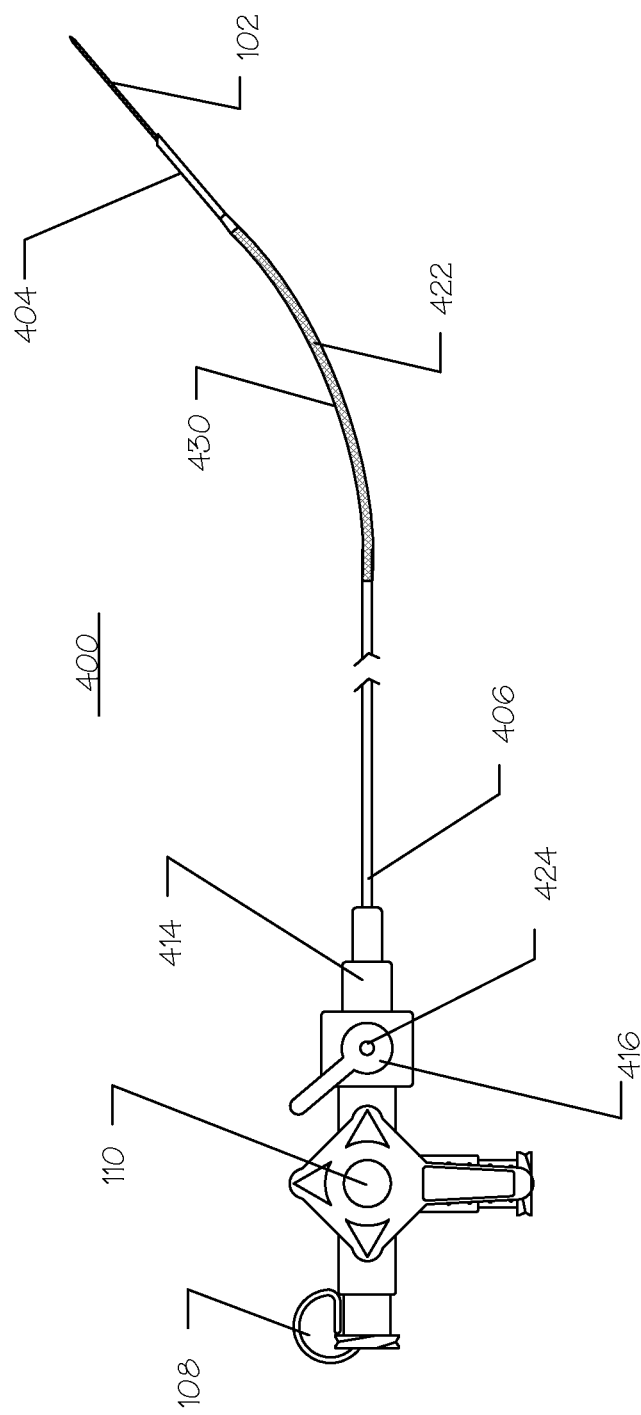
FIG. 5 illustrates a side view of the trans-septal punch of FIG. 4 wherein one of the pull-wires is placed in tension causing the distal flexible region of the punch to deflect into an arc away from the longitudinal axis of the punch.

FIG. 5 illustrates a side view of the punch assembly 400 wherein the deflecting lever 416 has been withdrawn proximally causing increased tension in one of the deflecting wires 412, causing the flexible region 430 to bend 422 out of the longitudinal axis. The punch assembly 400 further comprises the obturator wire 102, the obturator wire grasping tab 108, the stopcock 110, the deflecting lever 416, an axis cylinder 424, the hub 414, the outer tube 406, the inner tube 404, and the bend 422.

Referring to FIG. 5, the deflecting lever 416 has been moved proximally and the axis cylinder 424 causing the top deflecting wire 412 to be placed in tension while the bottom deflecting wire 412 is relaxed. The deflecting wires 412 are affixed at their distal end to the outer tube 406 or the inner tube 404 at a point substantially at or beyond the distal end of the flexible region 420. The distal fixation point (not shown) of the deflecting wires 412 is off-center from the axis of the outer tube 406 or inner tube 404. When uneven tension is created in the opposing deflecting wires 412, the uneven tension on the distal end of the punch 400 causes the bendable region 430 to undergo deflection into a curve or bend 422. Similarly, forward movement of the deflecting lever 416 will place the bottom deflecting wire 412 in tension while the upper deflecting wire 412 will be relaxed, causing the punch 400 to undergo a bend in the opposite direction (downward). The deflecting lever 416 can further comprise a ratchet and lock, a friction lock, a spring-loaded return, or other features to hold position or cause the lever and the bendable region 430 to return to a neutral deflection configuration (substantially straight). The spring nature of the outer tube 406 and the bendable region 430 can advantageously be used to cause a return to neutral once the deflection force is removed from the deflecting lever 416. The stylet or obturator wire 102 can be withdrawn or extended to expose or protect (respectively) the distal end of the inner tube 404 which can be sharpened or blunted. The obturator wire 102 can further be used as the primary punch, especially if the distal tip of the obturator wire 102 is sharpened. If the obturator wire 102 is used as the primary punch, the proximal end of the inner tube hub is fitted with a Tuohy-Borst or other hemostatic valve to permit the obturator wire 102 to remain in place. In this embodiment, sidearms affixed proximal to the proximal end of the punch, and operably connected to the central lumen, serve to permit pressure monitoring and dye contrast injection without compromising hemostasis or air entry into the punch assembly 400.

Figure 6:
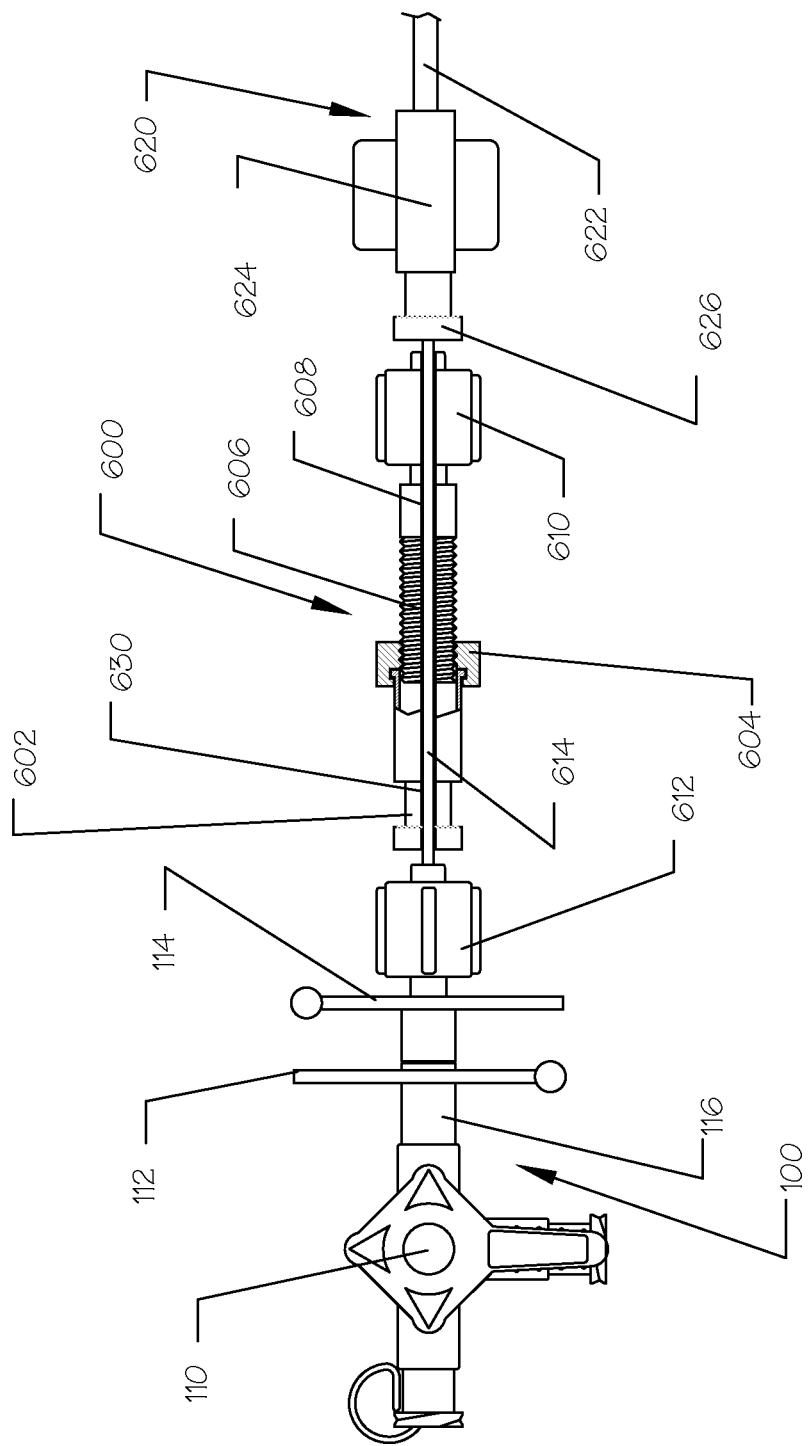
FIG. 6 illustrates an adjustable, spacer, which sets and maintains the distance between the distal end of the punch hub and the proximal end of a guide catheter hub.

FIG. 6 illustrates a side view of an adjustable spacer 600 interconnecting a guide catheter 620 and a punch assembly 100. The spacer 600 further comprises a proximal connector 602, a rotating nut 604, an inner telescoping tube 608, a threaded region 606, a distal locking connector 610, and an outer telescoping tube 614. The guide catheter further comprises a tube 622, a hub 624, and a proximal connector 626. The punch assembly 100 further comprises the stopcock 110, the distal rotating locking connector 612, the inner tube pointer 112, the outer tube pointer 114, and the inner tube hub 116. The spacer 600 can comprise an optional slot 630.

Referring to FIG. 6, the punch assembly 100 is inserted through the central lumen of the adjustable spacer 600. The distal end of the punch assembly 100 is then inserted through the central lumen of the guide catheter 620. The hub 624 of the guide catheter 620 is affixed to the proximal end of the guide catheter tube 622. The distal end of the hub 624 comprises a female Luer lock connection, which is bonded to, or integrally affixed to the hub 624. The hub 624 can further comprise a seal or hemostasis valve such as a Tuohy-Borst fitting. The punch 100 hub 116 is terminated at its distal end by a swivel male Luer lock connector 612. The adjustable spacer 600 comprises an outer telescoping tube 614, shown in partial cutaway view that is terminated at its proximal end with a female Luer lock 602. The proximal end of the outer telescoping tube 614 has a flange that permits rotational attachment of the rotating nut 604, shown in partial cutaway view, so that the rotating nut is constrained in position, longitudinally, relative to the outer telescoping tube 614 but is free to rotate. The inner telescoping tube 608 is affixed at its distal end with a swivel male Luer connector 610, or equivalent. The proximal end of the inner telescoping tube 608 is affixed to, or comprises, the integral threaded region 606. The threaded region 606 mates with the internal threads on the rotating nut 604. As the rotating nut 604 is rotated, either manually or by an electromechanical device, it moves forward or backward on the inner telescoping tube 608 and threaded region 606 thus changing the space between the hub 116 of the punch 100 and the proximal end of the hub 624 of the guide catheter 620. The system is preferably set for spacing that pre-sets the amount of needle or stylet travel. In an embodiment, the rotating nut 604 comprises a quick release that allows disengagement of the inner telescoping tube 608 from the outer telescoping tube 614 so that collapse is permitted facilitating the tissue punching procedure of advancing the punch 100 distally relative to the hub 624. The system further comprises hemostatic valves at some, or all, external connections to prevent air leaks into the punch 100. The telescoping tube 608 can be set to disengage from the outer telescoping tube 614 to allow for longitudinal collapse so that the punch 100 can be advanced distally to provide its tissue punching function. In another embodiment, the spacer 600 comprises the slot 630 that permits the spacer to be removed sideways off the punch 100. The slot 630 is wide enough to allow the outer tube 106 to fit through the slot 630 so the spacer 600 can be pulled off, or removed from, the punch 100 prior to the punching operation. Thus, the slot 630 can be about 0.048 to 0.060 inches wide and extend the full length of the spacer 600. With the slot 630, the spacer 600 comprises a generally "C-shaped" lateral cross-section. The spacer 600 can further comprise a slot closure device (not shown) to prevent inadvertent removal of the punch 100.

In another embodiment, the threaded region 606 and the rotating nut 604 are replaced by a friction lock on telescoping tubes, a ratchet lock, or other suitable distance locking mechanism. In yet another embodiment, a scale or series of markings (not shown) is incorporated into the adjustable spacer 600 to display the exact distance between the proximal end and the distal end of the spacer 600. In another embodiment, the proximal end and the distal end of the spacer 600 do not comprise one or both of the female Luer lock 602 or the rotating male Luer lock 610. In this embodiment, the spacer 600 provides positional spacing but does not affix the punch 100 to the guide catheter 620 so that the two devices move longitudinally as a unit. In another embodiment, the pull wires 412 of FIG. 4, which are strong in tension but cannot support compression are replaced by one or more control rods, which are flexible but which have column strength. Thus, deflection can be generated by imparting either tension on the control rod or compression and such tension and compression is capable of deflecting the distal tip of the punch 400 without the need of a separate control rod to impart tension in the other direction. The inner tube hub 116 is terminated at its proximal end by a female Luer, Luer lock, threaded adapter, bayonet mount, or other quick release connector. The quick connect or female Luer can be releasably affixed to a hemostasis valve, other stopcock, pressure transducer system, "Y" or "T" connector for pressure and radiopaque contrast media infusion, or the like.

In another embodiment, a vacuum line can be connected to a port affixed to the proximal end of the punch. The port can be operably connected to a bell, cone, or other structure at [he] the distal end of the punch by way of a lumen, such as the central lumen of the inner tube or an annulus between the intermediate and outer tube, within the punch. By application of a vacuum at the proximal end of the punch, the distal structure can be releasably secured to the atrial septum prior to punching through. In another embodiment, a corkscrew structure projects out the distal end of the punch and is operably connected to a knob or control at the proximal end of the punch by way of a control rod slidably or rotationally free to move within a lumen of the punch. The corkscrew structure can be screwed into tissue to releasably secure the distal end of the punch to the tissue, for example, to enhance stability of the punch prior to, during, or after the punching operation.

Referring to FIG. 1, in another embodiment, the inner tube 104, the outer tube 106, or both, are fabricated from shape memory nitinol. In this embodiment, electrical energy can be applied to the pre-bent regions of the inner tube 104, the outer tube 106, or both. Upon application of electrical energy, Ohmic or resistive heating occurs causing temperature of the tubes to increase. The nitinol changes its state from martensitic to austenitic, with the increase in temperature, and can assume a pre-determined configuration or stress state, which is in this case curved. The austenite finish temperature for such a configuration is approximately 40 degrees centigrade or just above body temperature. In yet another embodiment, the austenitic finish temperature can be adjusted to be approximately 28 to 32 degrees centigrade. The punch 100 can be maintained at room temperature where it is substantially martensitic and non-rigid. Upon exposure to body temperatures when it is inserted into the core lumen of the guide catheter, it will assume its austenitic shape since body temperature is around 37 degrees centigrade. This can cause the punch 100 to curve from substantially straight to substantially curved. In this configuration, only a single tube, either the inner tube 104 or the outer tube 106 is necessary, but both tubes, while potentially beneficial, are not required.

The punch can be used to create holes in various structures in the body. It is primarily configured to serve as an articulating or variable deflection Brockenbrough needle. However, the steerable punch can be used for applications such as transluminal vessel anastomosis, biopsy retrieval, or creation of holes in hollow organs or lumen walls. The punch can be used in the cardiovascular system, the pulmonary system, the gastrointestinal system, or any other system comprising tubular lumens, where minimally invasive access is beneficial. The punch can be configured to be coring or non-coring in operation, depending on the shape of the distal end and whether an obturator or the circular hollow end of the punch is used to perform the punching operation. In the coring configuration, a plug of tissue is removed, while in the non-coring configuration, substantially no tissue is removed from the patient. The punch facilitates completion of transseptal procedures, simplifies routing of the catheters, minimizes the chance of embolic debris being dislodged into the patient, and improves the ability of the cardiologist to orient the punch for completion of the procedure. The punch of the present invention is integral and steerable. It is configured to be used with other catheters that may or may not be steerable, but the punch disclosed herein does not require external steerable catheters or catheters with steerability to be steerable as it is steerable or articulating on its own. The punch is capable of bending and unbending a practically unlimited number of times. The punch is especially useful with catheters that are not steerable since the punch comprises its own steering system.

The present invention may be embodied in other specific forms without departing from its spirit or essential characteristics. The described embodiments are to be considered in all respects only as illustrative and not restrictive. For example, the deflecting wires 412 can be replaced by an electromechanical actuator and external control unit. The scope of the invention is therefore indicated by the appended claims rather than the foregoing description. All changes that come within the meaning and range of equivalency of the claims are to be embraced within their scope.

I claim:

1. A transseptal punch system for penetrating the atrial septum of a patient, said system comprising:
   a guide catheter adapted for insertion into the right atrium of a patient's heart, said guide catheter characterized by a distal end, and proximal end, and a guide catheter lumen extending from the distal end to the proximal end;
   a transseptal punch, said transseptal punch having a distal end and a proximal end, said transseptal punch fitting within the guide catheter lumen and being longitudinally advanceable within the guide catheter, said punch comprising:
      an outer tube, said outer tube characterized by a distal end and a proximal end, and an outer tube lumen extending from the distal end to the proximal end thereof, said outer tube having a flexible region near the distal end of the outer tube;
      a control rod disposed within the outer tube, said control rod characterized by a distal end and a proximal end;
      wherein the control rod is fixed to the distal end of the outer tube; and
   an inner tube fixed to the distal end of the outer tube, said inner tube having a sharp point for penetrating the atrial septum of the patient.

2. The system of claim 1 wherein:
   the control rod is fixed to the distal end of the outer tube at a point distal to the flexible region.

* * * * *